United States Patent [19]
Ranes et al.

[11] Patent Number: 6,133,448
[45] Date of Patent: Oct. 17, 2000

[54] NITRATION SYSTEM, AND METHOD FOR NITRATION OF AROMATIC COMPOUNDS

[75] Inventors: Eli Ranes, Halden; Jan Bakke, Hommelvik, both of Norway

[73] Assignee: Norsk Hydro ASA, Oslo, Norway

[21] Appl. No.: 09/242,895

[22] PCT Filed: Aug. 22, 1997

[86] PCT No.: PCT/NO97/00223

§ 371 Date: Feb. 26, 1999

§ 102(e) Date: Feb. 26, 1999

[87] PCT Pub. No.: WO98/08786

PCT Pub. Date: Mar. 5, 1998

[30] Foreign Application Priority Data

Aug. 28, 1996 [NO] Norway ................................ 963603

[51] Int. Cl.[7] .................. C07D 211/72; C07D 215/00
[52] U.S. Cl. ........................... 546/304; 546/152
[58] Field of Search ..................... 546/304, 152

[56] References Cited

U.S. PATENT DOCUMENTS

| | | | |
|---|---|---|---|
| 5,616,818 | 4/1997 | Pirkl et al. | 568/932 |
| 5,945,537 | 8/1999 | Sikkema | 546/307 |

FOREIGN PATENT DOCUMENTS

| | | |
|---|---|---|
| 174462 | 1/1994 | Norway . |
| 93/23352 | 11/1993 | WIPO . |

OTHER PUBLICATIONS

Arnestad et al., "Direct Nitration of Pyridine and Substituted Pyridine", Acta Chemica Scandinavica, vol. 50, Jun. 1996, pp. 556–557.

Bakke et al., "Nitration of pyridine by dinitrogen pentaoxide in sulfur dioxide: investigation of the reaction mechanism", J. Chem. Soc. Perkin Trans, vol. 2, 1995, pp. 1211–1215.

Bakke et al., "Dinitrogen Pentoxide–Sulfur Dioxide, a New Nitration System", Acta Chemica Scandinavica, vol. 48, 1994, pp. 181–182.

Taylor, "Nitration of Biphenyl by Nitronium Borofluoride", Tetrahedron Letters, vol. 49, 1966, pp. 6093–6095.

Chemical Abstracts, vol. 91, No. 13, Sep. 24, 1979, (Columbus, Ohio, USA), p. 584, The Abstract No. 107978f, SU, 662551 A, (Gidaspov B.V. et al.) May 15, 1979.

Zielinska et al., "Reaction of Dinitrogen Pentoxide with Fluoranthene" J. Am. Chem. Soc., vol. 108, 1986, pp. 4126–4132.

Albright, et al., "Recent Laboratory and Industrial Developments", American Chemical Society, Nitration, Jun. 18, 1996, pp. 134–150.

*Primary Examiner*—Deborah C. Lambkin
*Attorney, Agent, or Firm*—Wenderoth, Lind & Ponack, L.L.P.

[57] ABSTRACT

This invention relates to a new nitration system, and a new method for nitration of aromatic compounds. The nitration system comprises dinitrogen pentaoxide dissolved in an organic solvent, and after having generated an intermediate therein, this reaction mixture is poured into a water solution of a selected nucleophile. The nucleophile preferably comprises a hydrogen sulphite ion, sulphite ion or sulphur dioxide.

5 Claims, No Drawings

NITRATION SYSTEM, AND METHOD FOR NITRATION OF AROMATIC COMPOUNDS

This application is a 371 of PCT/NO97/00223 Aug. 22, 1997.

This invention relates to a new nitration system, and a new method for nitration of aromatic compounds.

Aromatic nitro compounds are of great importance, both as such and as starting material for the production of pharmaceuticals, dyestuff, pesticides and other important products. It is therefore of general interest both to optimise the existing nitration methods and to invent new ones.

Nitration of aromatic compounds is mainly performed by the use of a mixture of nitric and sulphuric acid (the "mixed acid" method) or by the use of nitric acid itself. For many aromatic compounds a satisfactory yield is obtained by the use of these comparatively cheap reagents. However, the use of strong acids makes these methods less suitable for the nitration of compounds containing acid sensitive groups. Furthermore, the nitration of several aromatic compounds gives only low or no yields by these reagents, This is the case for several hetero aromatic substance classes, for instance for pyridine and substituted pyridines.

Another system reported for the nitration of aromatic compounds is dinitrogen pentaoxide ($N_2O_5$) dissolved in $HNO_3$ (U.S. Pat. No. H-447 and DE-2435651). Dinitrogen pentaoxide has gained technical importance after the invention of new methods for its production (EP-295878, U.S. Pat. No. 4,432,902 and U.S. Pat. No. 4,525,252). Dinitrogen pentaoxide in $HNO_3$ is more reactive than nitric acid or nitric acid/sulfuric acid. Less reactive aromatic compounds may therefore be successfully nitrated by this system. However, the presence of nitric acid may be detrimental to acid sensitive compounds. Furthermore, several compounds, for instance pyridine and substituted pyridines, are nitrated in very low yields even by this system (J. Bakke and I. Hegbom, *Acta Chem. Scand.*, 48 (1994) 181).

Pyridine and several substituted pyridines are nitrated in yields lower than 5% by the methods referred to above. In our Norwegian Patent NO-C-174 462 the inventors described a method for nitration of aromatic compounds by using dinitrogen pentaoxide in sulphur dioxide ($SO_2$). This method was particularly advantageous for pyridine systems. Good yields were obtained for a series of these compounds. However, the use of sulphur dioxide, especially as a solvent, has several disadvantages such as low reaction temperatures and technical difficulties in handling large amounts of liquid sulphur dioxide. The inventors later found that it was not necessary to use liquid sulphur dioxide as a solvent for the successful outcome of the reaction. Conventional organic solvents could be used together with only a minor proportion of sulphur dioxide. The experiments showed that approximately two molecules of sulphur dioxide per molecule of pyridine were needed in the reaction mixture to obtain as good results as those obtained when liquid sulphur dioxide was used for the reaction (NO-A-950367). Even though, Norwegian patent application no. 950367 discloses a nitration system advantageous over the one disclosed in Norwegian patent no. 174462, it still involves a need of some sulphur dioxide. By using modern equipment application of sulphur dioxide can be made safe. However, using sulphur dioxide makes the operations cumbersome.

Thus, the main object of this invention is to provide a nitration system and a method for nitration of aromatic compounds, in particular pyridine and substituted pyridines, where the disadvantages by using sulphur dioxide together with an organic solvent, are omitted.

This and other objects of the invention are solved as characterised by the features stated in the attached claims.

The inventors have found that the presence of sulphur dioxide in the reaction mixture containing the pyridine compound and dinitrogen pentaoxide is not necessary for the formation of a nitrated pyridine compound. Instead, the reaction between the pyridine compound and dinitrogen pentaoxide can be carried out in a standard organic solvent, for instance tetrahydrofuran (THF), nitromethane ($CH_3NO_2$) or one of the other solvents used in Norwegian patent NO-A-950367. After formation of a N-nitropyridinium ion (2), the organic solution is mixed with water containing a nucleophile such as the hydrogen sulphite ion ($HSO_3^-$), sulphite ion ($SO_3^{2-}$) or sulphur dioxide.

For the reaction, a pyridine compound (1) is added to a solution of dinitrogen pentaoxide in an organic solvent. The addition should be made at temperatures from $-30°$ C. to $15°$ C. The addition should be made during 5–30 minutes for a typical run in Table 1. After 5–30 minutes, the reaction mixture is poured into a water solution of the selected nucleophile. The nucleophile should be selected from the ones in Table 1 and in concentrations from 0.1 to 5M but always such that there is an excess of nucleophile as compared to the starting amount of pyridine compound. After from 1–5 hours the water phase is extracted and the nitrated pyridinium compound isolated by standard procedures.

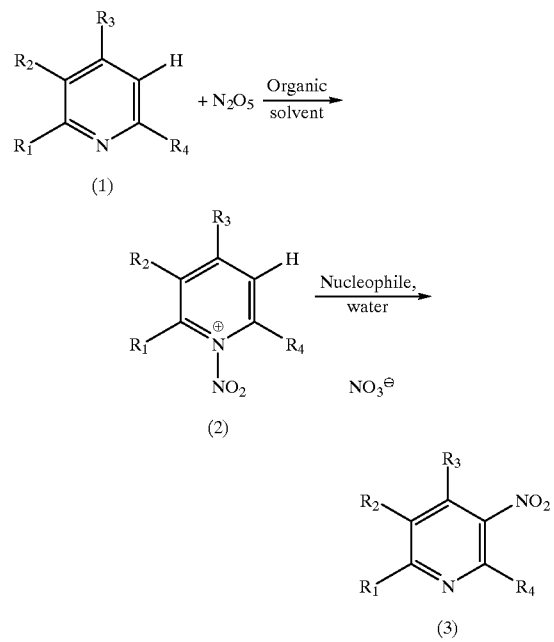

For (1), (2) and (3) $R_1$–$R_4$ are in dependent of each other and being hydrogen, $C_1$–$C_4$ alkyl, $C_1$–$C_4$ alkoxy or $C_1$–$C_4$ alkoxycarbonyl; and where $R_1$ and $R_2$ may together with the carbon atoms they are combined form an aromatic ring containing 6 carbon atoms.

In Table 1 we have given the results from the reaction of the product from pyridine with dinitrogen pentaoxide ((2), $R_1$=$R_2$=$R_3$=$R_4$=H) with a series of nucleophiles dissolved in water. In Table 2 is given the results from the reaction of the complex (2) between a series of pyridine systems and dinitrogen pentaoxide with sodium hydrogen sulphite ($NaHSO_3$) in water. From Tables 1 and 2 it is evident that this new system for nitration of pyridine compounds gives as good results as those from the ones containing sulphur dioxide in the medium used for the reaction between the pyridine compound and dinitrogen pentaoxide (Norwegian Patent application NO-A-950367).

TABLE 1

Reaction of N-nitropyridinium nitrate with nucleophiles in water. [Pyridine] = 0.5M; [nucleophile] ~ 1.5M.

| [PyrH]/[N$_2$O$_5$] | Solvent[a] | Nucleophile | % Pyridine | % 3-Nitropyridine |
|---|---|---|---|---|
| 1/2 | THF | SO$_2$[b] | not analysed | 33 |
| 1/1 | CH$_3$CN | SO$_2$[b] | 16 | 15 |
| 1/2 | CH$_3$NO$_2$ | SO$_2$[c] | 13 | 56 |
| 1/1.8 | CH$_3$NO$_2$ | NaHSO$_3$ | 3 | 65 |
| 1/2 | CH$_3$NO$_2$ | NaHSO$_3$[d] | 1 | 68 |
| 1/2 | THF | Na$_2$SO$_3$ | 1 | 23 |
| 1/1.3 | THF | NaHSO$_3$ | 41 | 30 |

[a] For the formation of N-nitropyridinium nitrate from pyridine and N$_2$O$_5$. [N$_2$O$_5$] = 1.0M.
[b] Gaseous SO$_2$ was passed into the water phase for 30 min. prior to the reaction with N-nitropyridinium nitrate.
[c] SO$_2$(l) (25 mL) was poured into the water phase (100 mL) immediately after adding the N-nitropyridinium nitrate solution.
[d] Concentration of NaHSO$_3$ twice that of the previous run.

TABLE 2

Nitration of pyridine, substituted pyridines and quinolines. Substrate and N$_2$O$_5$ were reacted in CH$_3$NO$_2$ (25 mL) and the product poured into water (100 mL) containing NaHSO$_3$ (10 g).

| Substrate | Recovered substrate (%) | Yield of 3-nitro derivative (%) |
|---|---|---|
| Pyridine | 3 | 65 |
| Isoquinoline | 11 | 32 |
| Quinoline | 50 | 8 |
| 4-Acetylpyridine[a] | 11 | 58 |
| 4-Metylpyridine | 10 | 32 |

[a] [NaHSO$_3$] = 0.5M.

This new nitration system is advantageous over the previously used reaction systems as there is no longer a need to use the noxious gas sulphur dioxide. While the application of sulphur dioxide can be made safe by the use of modern equipment, its use makes the operations cumbersome. By this new reaction system, nucleophilic reactants in form of powders, for instance sodium sulphite (Na$_2$SO$_3$) and sodium hydrogen sulphite (NaHSO$_3$) can be used. These powders are easily manipulated at an industrial scale and the use of equipment for the handling of noxious gases is no longer necessary. These reactants will be easily dissolved in the water phase used for reaction with the pyridine—dinitrogen pentaoxide.

On the other hand, a choice of reactants and reaction conditions is now possible for the nitration reaction. If—for some reason—sulphur dioxide is the chosen nucleophilic reagent, it is not necessary to dissolve it in the organic solvent used for the reaction between the pyridine compound and dinitrogen pentaoxide as—surprisingly—it is only necessary to have it dissolved in the water phase.

If the organic solvent used for the reaction with dinitrogen pentaoxide is immiscible with water, the formed nitro compound will dissolve in this and thus be easily separated from the aqueous phase.

What is claimed is:

1. Method for nitration of aromatic compounds, characterized in that an aromatic compound is added to a solution of dinitrogen pentaoxide in an organic solvent, and the provided reaction mixture is thereafter added into water comprising a nucleophile.

2. Method according to claim 1, characterized in that the reaction of the aromatic compound in the solution of dinitrogen pentaoxide and organic solvent is performed at temperatures from −30° to 15° C. during a period of 5 to 30 minutes, before added to a mixture of water and a nucleophile in concentrations of 0.1 to 5M for a period of 1 to 5 hours.

3. Method according to claim 1, characterized in that the organic solvent being an ether, substituted hydrocarbon or amide, and the nucleophile comprises a hydrogen sulphite ion, sulphite ion or sulphur dioxide.

4. Method according to claim 1, characterized in that the aromatic compounds which are nitrated are pyridine, substituted pyridines or quinolines.

5. Method according to claim 1, characterized in that the organic solvent used is tetrahydrofuran (THF) or nitromethane.

* * * * *